United States Patent
Hilsen

Patent Number: 5,884,628
Date of Patent: Mar. 23, 1999

[54] SNORING DEVICE

[76] Inventor: Kenneth Hilsen, 33 Brodil Ct., Closter, N.J. 07624

[21] Appl. No.: 818,354

[22] Filed: Mar. 17, 1997

[51] Int. Cl.$^6$ ........................................ A61F 5/56
[52] U.S. Cl. ............................. 128/848; 128/859; 602/902
[58] Field of Search ........................... 128/848, 859–862; 2/2, 246; 602/902; 433/6, 7, 18, 215

[56] References Cited

U.S. PATENT DOCUMENTS

| | | |
|---|---|---|
| 2,705,492 | 4/1955 | Chandler. |
| 2,827,899 | 3/1958 | Altieri ..................................... 128/862 |
| 3,457,916 | 7/1969 | Wolicki ................................... 128/862 |
| 3,997,162 | 12/1976 | Scullin. |
| 4,055,895 | 11/1977 | Huge. |
| 4,173,219 | 11/1979 | Lentine. |
| 4,304,227 | 12/1981 | Samelson. |
| 4,376,628 | 3/1983 | Aardse .................................... 128/861 |
| 4,396,373 | 8/1983 | Dellinger. |
| 4,505,672 | 3/1985 | Kurz. |
| 4,901,737 | 2/1990 | Toone. |
| 5,035,613 | 7/1991 | Breads et al.. |
| 5,037,295 | 8/1991 | Bergersen. |
| 5,055,039 | 10/1991 | Abbatte et al.. |
| 5,082,007 | 1/1992 | Adell. |
| 5,145,364 | 9/1992 | Martz et al.. |
| 5,277,202 | 1/1994 | Hays. |
| 5,313,960 | 5/1994 | Tomasi. |
| 5,365,945 | 11/1994 | Halstrom. |
| 5,499,633 | 3/1996 | Fenton ..................................... 128/848 |
| 5,548,848 | 8/1996 | Huybrechts ............................. 128/862 |
| 5,611,355 | 3/1997 | Hilsen. |

FOREIGN PATENT DOCUMENTS 0 254 918  2/1988  Germany.

OTHER PUBLICATIONS

O.T. Altay et al., The Biological Effects of Implanted Magnetic Fields on the Bone Tissue of Dogs, *The International Journal of Oral & Maxillofacial Implants*, vol. 6 No. 3 pp. 345–349 (1991).

Carl J. Drago, Tarnish and Corrosion with the Use of Intraoral Magnets, *The Journal of Prosthetic Dentistry*, vol. 66 No. 4 pp. 536–540 (Oct. 1991).

*Primary Examiner*—Michael A. Brown
*Attorney, Agent, or Firm*—Stephen E. Feldman

[57] ABSTRACT

A device is disclosed that can be adapted to fit the dentitions of a user to prevent snoring. The device has a flexible, U-shaped upper member and a flexible, U-shaped lower member each of which have releasable fastening means affixed to them enabling a user to easily and readily adjust the two members relative to one another so as to keep the user's airway passage open and thereby prevent snoring. A moldable material is provided in each of the members so that a user can make an impression of the user's upper and lower dentitions which are then contained permanently in the moldable material which material remains flexible on setting. This assures a snug and comfortable fit for the user when the upper and lower members are inserted into the user's mouth.

6 Claims, 1 Drawing Sheet

SNORING DEVICE

FIELD OF INVENTION

This invention relates to a device that prevents interference with normal breathing during sleeping. More particularly, this invention relates to a device that alleviates snoring and which the user can insert into their mouth and then adjust it to a proper position.

1. Background of the Invention

Obstructive sleep apnea and obstructive breathing (snoring) are caused mainly by the collapse of the airway at the back of the throat. This occurs when the tongue falls to the back of the throat and other oral structures in the throat collapse to block the breathing airway. In snoring, the air forcibly passes through the airway causing loud vibrations.

2. Description of the Prior Art

Various devices for preventing or decreasing snoring are known in the prior art. For example, Strickland, in U.S. Pat. No. 3,434,470, discloses an oral device to inhibit snoring wherein the device includes a plate adapted to be placed within the mouth in the U-shaped space defined by the upper teeth. The plate has a mounting structure which releasably grips the upper teeth to reduce the effective volume of air flowing into and out of the mouth. The decreased air flow resulting from the presence of the plate inhibits snoring.

Shapiro, et al, in U.S. Pat. No. 5,117,816, discloses a device that has a mouthpiece formed from a moldable thermoplastic material having an upper surface portion that substantially covers the entire maxillary (upper) dentition and a lower surface portion that contacts substantially the entire mandible (lower) dentition of a user's mouth. The lower surface portion includes a downwardly extending flange intended to extend into the lingual (tongue side of the teeth) vestibule of a user in order to maintain a forward posture of the lower jaw. An airway passage is centrally disposed to permit adequate breathing through the mouthpiece if nasal blockage is present. An anterior portion of the mouthpiece surrounding the airway passage is concave to enable proper positioning of a user's tongue. The device includes a handle which is used to aid in protecting the user during the initial fitting process. To insure the integrity of the airway slot during the fitting process, the handle includes a specially shaped extension portion that can be frictionally secured in the airway passage while the entire mouthpiece is maneuvered by a remote upper portion of the handle.

Samelson, in U.S. Pat. No. 4,304,277, discloses a device which is an integrally molded body. The device provides dental engaging portions and a rearwardly open central socket that cooperates with the forward portion of a user's tongue in such a manner as to draw the tongue forward to increase the unobstructed dimension of the nasal breathing passage. When operatively positioned within the mouth, some of the user's upper and lower teeth enter the recesses provided by the device. The tongue is held in the socket by negative pressure developed in the socket. When the tongue is thus held, it draws the body of the tongue forward of its usual restive position behind the lower teeth and adjacent the soft palate, the uvula and the posterior pharyngeal wall thereby increasing the dimension of the air flow passage through the nasopharynx to facilitate nasal breathing.

Toone, in U.S. Pat. No. 4,901,737, discloses a rigid, generally V-shaped wedge molded to the entire mandibular dentition and a portion of the maxillary dentition. It is completely open in front and open at the top (across the palatal arch). The mandibular incisional edge is embedded with a lip extending over the labial surface of the mandibular incisors, over the lingual surfaces of all mandibular teeth, and downwardly into the lingual vestibule. It covers the palatal surfaces of the maxillary bicuspids and molars and extends onto the palate. The lack of full palatal coverage provides space for the tongue which rests in its normal position. The device comprises a pair of generally V-shaped spacer members disposed in a spaced apart, side by side relationship. In an adjustable embodiment, each of the spacer members are formed in two pieces; i.e., an upper and a lower portion. A threaded adjustment rod, having one end disposed within one of the portions and the other end bearing against the other portion, is used to adjust the relative positions of the upper and lower portions. The range of adjustment permitted by the rod is relatively limited.

The present invention provides a device that can prevent snoring. The device is less bulky, is flexible and is adjustable to a degree that the above-described references are not. In addition, the device of the invention can be adjusted and form fitted by the user, is of simple design, and is more comfortable than the devices disclosed by the prior art.

SUMMARY OF THE INVENTION

The device of the present invention can be readily adapted to fit any particular user's mouth for the prevention of snoring, and is meant to be fitted and adjusted by the user. In general, the device of the present invention comprises: an upper and lower flexible mounting means each of which is a substantially U-shaped, unitary, integral unit having a front wall; a rear wall; an inner bight surface portion; an outer bight surface portion, said inner and outer bight surface portions interconnecting said front and rear walls to define a U-shaped dentition cavity therebetween; releasable fastening means affixed to said outer bight surface portions; and a moldable material that contains the impressions of the upper and lower dentitions of a user.

The upper and lower U-shaped mounting means of the device of the invention form flexible mouthpieces typically manufactured from flexible materials that remain flexible that can be commercially obtained in most sports stores or from specialty mouthpiece makers such as Shields, Inc. in Tonowanda, N.Y.

The releasable fastening means that are affixed to the upper and lower mounting means can be provided from commercially available materials such as interlocking hook fastening materials available under the DUAL-LOK trademark by 3M Corporation. These releasable fastening materials can be affixed to the outer bight surface portions of the legs of the upper and lower U-shaped mounting means by any suitable, conventional means such as using appropriate glues, stitching, and the like. For example, using strong thread such as nylon is particularly effective. The stitching is done between the mushrooms of the DUAL-LOK to hold it to the mounting means.

After the releasable fastening material has been affixed to both the upper and lower U-shaped, flexible mounting means, the user can adapt each mounting means to fit the user's particular upper and lower dentition profiles. This can be readily accomplished by the user by applying a layer of a moldable material such as a flexible dental acrylic, onto the inner bight surface portions of the mounting means to engage the user's dentitions, holding the mounting means in place for a period of time sufficient to permit the moldable material to harden and cure (usually for about 5 minutes), but remain flexible, and retain the dentition impressions. In this way, one can provide for oneself upper and lower mounting means that contain a personalized, permanent impression profile of one's upper and lower dentitions and that also have the releasable fastening means permanently affixed to them. The flexibility of the moldable material permits ease in obtaining a good quality fit.

Although those acrylic materials generally used by dentists to obtain dentition profiles and impressions can be employed by the user to create the user's personalized dentition impressions and profile, a proprietary acrylic material available from Shields, Inc., Tonowanda, N.Y. is preferred for its ease of application and use. Another such material used which is used by dentists is COE-COMFORT™ made by G. C. AMERICA, INC., Chicago, Ill.

BRIEF DESCRIPTION OF THE DRAWING

The device of the invention will become more apparent from the ensuing description when considered together with the accompanying drawing wherein.

DETAILED DESCRIPTION OF THE INVENTION

The upper and lower mounting means of the invention are substantially similar, the ensuing description is directed to only one mounting means it being expressly understood that this description is intended to encompass both the upper and the lower mounting means comprising the device of the invention. The upper and lower mounting means may have slightly different configurations because of the slight differences in the shape of the lower and upper jaws, and the inside space between the teeth and the inner wall of the mouth, the buccal vestibule.

Figure 1:
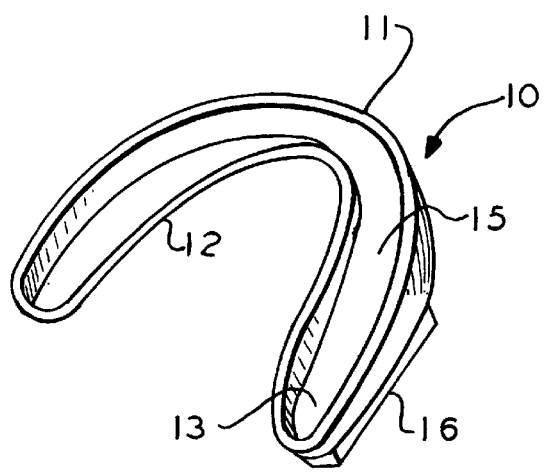
FIG. 1 is a simplified perspective view illustrating the flexible mounting means of the device of the invention.
Figure 2:
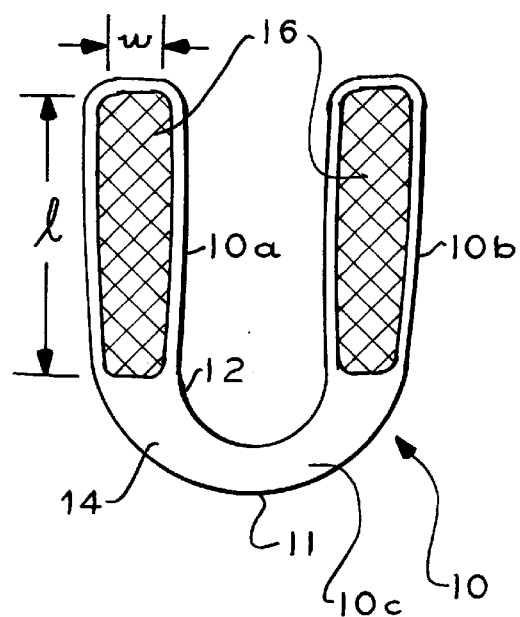
FIG. 2 is a plan view of the mounting means shown in FIG. 1.

Turning now to the drawing, wherein like reference numerals identify like parts, it can be seen from FIGS. 1 and 2 that the flexible mounting means comprising the device of the invention is a substantially U-shaped, unitary, integral member, generally identified by reference numeral 10, having spaced apart, opposed, elongated legs 10a and 10b; a curvilinear section 10c connecting elongated legs 10a and 10b; front and rear walls 11 and 12, respectively; and inner and outer bight surface portions 13 and 14, respectively, which interconnect the front and rear walls 11 and 12 to define a U-shaped dentition engaging cavity therebetween.

Figure 4:
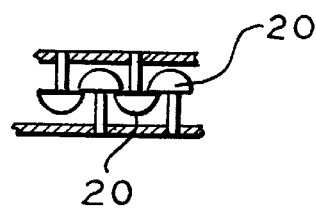
FIG. 4 is a detailed view of the DUAL-LOK fastener.

The flexible mounting means 10 has affixed thereto releasable fastening means 16 shown in cross hatching in FIG. 2. As mentioned above, the releasable fastening means 16 are preferably interlocking mushrooms 20 available under the DUAL-LOK trademark by 3M Company, as shown in detail in FIG. 4. It is understood that equivalent materials can be used. As can be seen in FIG. 2, the releasable fastening means 16 is affixed so as to be disposed along the full length "I" and the full width "w" of each of the elongated legs 10a and 10b.

Figure 3:
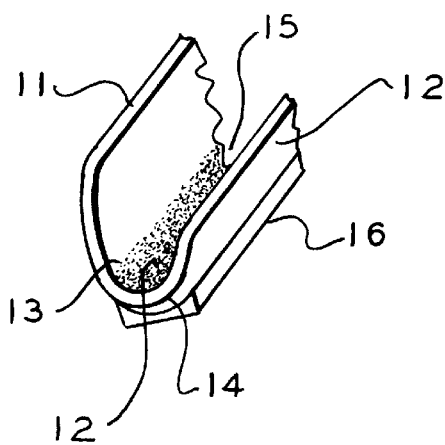
FIG. 3 is a fragmentary, simplified cross-sectional view of the mounting means of FIG. 1.

Once the releasable fastening means 16 have been firmly secured to the mounting means 10, the user can proceed to adapt the upper and lower mounting means to fit the personal profile of the user's upper and lower dentitions. The user can readily accomplish this by applying to the inner bight surface portion 13 of the U-shaped dentition cavity 15 a layer of moldable material such as a dental acrylic that remains flexible on setting, as indicated by reference numeral 17 in FIG. 3, in an amount sufficient to receive and create dentition impressions. The user then places the mounting means in the user's mouth so that the moldable material 17 engages the user's dentitions to a degree that will permit the moldable material to receive and retain an impression profile of the dentitions—the upper mounting means being placed to engage the user's upper dentitions and the lower mounting mean s being placed to engage the user's lower dentitions. Each of the mounting means is held in place by the user in engagement with the user's dentitions for a period of time sufficient for the moldable material 17 to harden or set so that it receives and retains the dentition impressions—usually for about 5 minutes.

After the user has created the user's personal dentition impressions in this way, the user can then insert the flexible mounting means to engage the user's upper and lower dentitions in a snug, close fitting relationship. This enables the user to easily and comfortably adjust the upper and lower flexible mounting means relative to one another until the user finds that position where the mounting means are most effective in overcoming the user's snoring.

Because of the nature of the interlocking material used for the releasable fastening means 16 and the flexibility of the upper and lower mounting means 10, it allows for a large degree of flexibility. Moreover, a shock absorbing characteristic is impaired to the device of the invention. This shock absorbing characteristic prevents the user's teeth from grinding.

In addition, the adjustability of the lower mounting means relative to the upper mounting means of the invention device covers a wide range permitting both forward and backward movement as well as side to side movement. This is accomplished because the nature of the releasable fastening means 16 permits the upper and lower mounting means to be readily detached from one another and repositioned by the user. Additionally, since the front and back portions of the lower jaw do not move together in a straight line or in the same plane, the nature of the releasable fastening means 16 compensates for such non-rectilinear movement. Therapeutic value is provided to the user since the releasable fastening means 16 permit the lower mounting means to be gradually moved and repositioned relative to the upper mounting means over a period of days or weeks until the user finds that position where the device prevents the user from snoring. In this way, the jaw muscles are gradually conditioned so that they can comfortably adjust to the position found by the user that prevents snoring.

The device of the invention permits a user to maintain his lower jaw in its normal position during sleep and allows the user to adjust the device to a more forward position, if necessary. Maintaining the lower jaw in its normal position or moving the lower jaw forward causes the airway to open thereby preventing snoring. This is a purely mechanical procedure that will be immediately effective, but which will revert to obstruction again as soon as the device is removed and not used. Thus, the device of the invention must be continuously in place during sleep in order to gain the above benefits. The invention permits the user himself to fit the device and adjust it to the correct position.

This device has been described as applicable to the prevention of snoring. However, it is understood that it may also be useful for the prevention of sleep apnea.

Although the device of the invention has been described with particularity and in some detail, it will be appreciated by those skilled in the art that changes and modifications can be made therein without departing from the scope and spirit of the invention.

What is claimed:

1. A user adaptable anti-snore device comprising:

an upper flexible member having a substantially curved shape and defining an upwardly oriented channel for receiving at least a portion of at least some of the upper teeth of a user, the upper member further defining opposed sides thereof;

a lower flexible member having a substantially curved shape and defining a downwardly oriented channel for receiving at least a portion of at least some of the lower teeth of a user, the lower member further defining opposed sides thereof; and, ready releasable, adjustable, connectors for releasably, adjustably joining the upper and lower members together, further comprising opposing surfaces of interlocking hook fastening material including opposing interlocking mushroom shaped members;

wherein said devise is constructed at least in part of a moldable material enabling said user to adapt, fit and adjust said device to fit upper and lower teeth of said user.

2. The device of claim 1 wherein said moldable material is a flexible material applicable by the user to said upwardly oriented channel and said downwardly oriented channel for containing impressions of said teeth for holding said device in position.

3. A method of substantially suppressing the snoring of a user comprising:

providing a user-adaptable anti-snore device that includes: an upper flexible member having a substantially curved shape and defining an upwardly oriented channel for receiving at least a portion of at least some of the upper teeth of said user, the upper member further defining opposed sides thereof; a lower flexible member having a substantially curved shape and defining a downwardly oriented channel for receiving at least a portion of at least some of the lower teeth of a user, the lower member further defining opposed sides thereof, and, readily releasable, adjustable, connectors for releasably, adjustably joining the upper and lower members together, further comprising opposing surfaces of interlocking hook fastening material including opposing interlocking mushroom shaped members; wherein said device is constructed at least in part of a moldable material enabling said user to adapt, fit and adjust said device to fit upper and lower teeth of said user; and, mounting said device in the mouth of said user.

4. A user-adaptable anti-sleep apnea device comprising:

am upper flexible member hang a substantially curved shape and defining an upwardly oriented channel for receiving at least a portion of at least some of the upper teeth of a user, the upper member further defining opposed sides thereof;

a lower flexible member having a substantially curved shape and defining a downwardly oriented channel for receiving at least a portion of at least some of the lower teeth of a user, the lower member further defining opposed sides thereof; and, readily releasable, adjustable, connectors for releasably, adjustably joining the upper and lower members together, further comprising opposing surfaces of interlocking hook fastening material including opposing interlocking mushroom shaped members;

wherein said devise is constructed at least in part of a moldable material enabling said user to adapt, fit and adjust said device to fit upper and lower teeth of said user.

5. The device of claim 4 wherein said moldable material is a flexible material appliable by the user to said upwardly oriented channel and said downwardly oriented channel for containing impressions of said teeth for holding said device in position.

6. A method of substantially suppressing the anti-sleep apnea of a user comprising:

providing a user-adaptable anti-sleep apnea device that includes: an upper flexible member having a substantially curved shape and defining an upwardly oriented channel for receiving at least a portion of at least some of the upper teeth of said user, the upper member further defining opposed sides thereof, a lower flexible member having a substantially curved shape and defining a downwardly oriented channel for receiving at least a portion of at least some of the lower teeth of a user, the lower member further defining opposed sides thereof; and, readily releasable, adjustable, connectors for releasably, adjustably joining the upper and lower members together, further comprising opposing surfaces of interlocking hook fastening material including opposing interlocking mushroom shaped members; wherein said devise is constructed at least in part of a moldable material enabling said user to adapt, fit and adjust said device to fit upper and lower teeth of said user; and, mounting said device in the mouth of said user.

* * * * *